(12) United States Patent
Sugiyama et al.

(10) Patent No.: US 9,429,579 B2
(45) Date of Patent: Aug. 30, 2016

(54) BLOOD ANALYSIS APPARATUS

(75) Inventors: Koji Sugiyama, Kyoto (JP); Tatsuo Kamata, Kyoto (JP); Takeshi Takagi, Kyoto (JP)

(73) Assignee: ARKRAY, INC., Kyoto (JP)

( * ) Notice: Subject to any disclaimer, the term of this patent is extended or adjusted under 35 U.S.C. 154(b) by 1107 days.

(21) Appl. No.: 12/311,175

(22) PCT Filed: Sep. 20, 2007

(86) PCT No.: PCT/JP2007/068313
§ 371 (c)(1),
(2), (4) Date: Apr. 13, 2010

(87) PCT Pub. No.: WO2008/035748
PCT Pub. Date: Mar. 27, 2008

(65) Prior Publication Data
US 2012/0094367 A1    Apr. 19, 2012

(30) Foreign Application Priority Data
Sep. 22, 2006  (JP) ................ 2006-256677

(51) Int. Cl.
| G01N 33/00 | (2006.01) |
|---|---|
| G01N 35/00 | (2006.01) |
| G01N 33/66 | (2006.01) |
| G01N 33/72 | (2006.01) |
| G01N 35/02 | (2006.01) |
| A61B 5/145 | (2006.01) |
| G01N 30/88 | (2006.01) |

(52) U.S. Cl.
CPC ............ G01N 33/66 (2013.01); G01N 33/723 (2013.01); G01N 35/026 (2013.01); A61B 5/14532 (2013.01); G01N 2030/8822 (2013.01); G01N 2800/042 (2013.01)

(58) Field of Classification Search
CPC .................. G01N 2030/8822; G01N 33/66; G01N 35/026
See application file for complete search history.

(56) References Cited

U.S. PATENT DOCUMENTS

| 5,348,649 A | 9/1994 | Mizuno et al. |
|---|---|---|
| 5,474,677 A | 12/1995 | Naka |

(Continued)

FOREIGN PATENT DOCUMENTS

| JP | S59-168371 A | 9/1984 |
|---|---|---|
| JP | S63-218864 A | 9/1988 |

(Continued)

OTHER PUBLICATIONS

Communication from European Patent Office for application No. 07807665.0 dated Oct. 29, 2009.

(Continued)

*Primary Examiner* — Nathan Bowers
(74) *Attorney, Agent, or Firm* — Studebaker & Brackett PC (57) ABSTRACT

The present invention relates to a blood analysis apparatus X for measuring concentrations of glucose and glycohemoglobin in blood. The blood analysis apparatus X is configured to perform the concentration measurement of the glucose and the glycohemoglobin by one sampling of blood 13. The blood analysis apparatus X is preferably configured to simultaneously carry out sample preparations for concentration measurement of the glucose and the glycohemoglobin by one sample preparation. The blood analysis apparatus X may be configured to perform dilution of a blood sample for measuring the glycohemoglobin and dilution of a blood sample for measuring the glucose using the same diluent.

24 Claims, 8 Drawing Sheets

(56) References Cited

U.S. PATENT DOCUMENTS

| | | |
|---|---|---|
| 6,670,192 B1 | 12/2003 | Galen et al. |
| 2005/0214161 A1 | 9/2005 | Gupta |
| 2006/0058301 A1* | 3/2006 | Zhu et al. ............... 514/241 |
| 2009/0321281 A1* | 12/2009 | Shinno et al. ............ 205/792 |

FOREIGN PATENT DOCUMENTS

| | | |
|---|---|---|
| JP | 02-159563 A | 6/1990 |
| JP | 05-005730 A | 1/1993 |
| JP | 09-033533 A | 2/1997 |
| JP | 09-178719 A | 7/1997 |
| JP | 10-227779 A | 8/1998 |
| JP | 2000-321281 A | 11/2000 |
| JP | 2000-346848 A | 12/2000 |
| JP | 2001-99838 A | 4/2001 |
| JP | 2005-148058 A | 6/2005 |

OTHER PUBLICATIONS

International Search Report mailed on Jan. 8, 2008.
Office Action issued in Japanese Application No. 2013-259236, dated Jan. 6, 2015.

* cited by examiner

```
........................................
PATIENT A : Glu=98mg/dL, MINOR=NO
(TIME OF FASTING) HbA1c=(CANCEL)  NORMAL
........................................
PATIENT B : Glu=145mg/dL , MINOR=YES
(TIME OF FASTING) HbA1c=6.7%    DIABETES
........................................
PATIENT C : Glu=115mg/dL , MINOR=NO
(TIME OF FASTING) HbA1c=6.1%   BOUNDARY
TYPE
........................................
```

FIG.4

| | |
|---|---|
| DIABETES TYPE | BLOOD GLUCOSE VALUE IN FASTING GREATER THAN OR EQUAL TO 126 mg/dL<br><br>BLOOD GLUCOSE VALUE IS GREATER THAN OR EQUAL TO 200 mg/dL AT ANY TIME |
| BOUNDARY TYPE | NUMERICAL VALUE NOT BELONGING TO NORMAL TYPE OR DIABETES TYPE |
| NORMAL TYPE | BLOOD GLUCOSE VALUE IN FASTING SMALLER THAN 110 mg/dL<br><br>HEMOGLOBIN A1C IS BETWEEN 4.3 AND 5.8% |

BLOOD ANALYSIS APPARATUS

TECHNICAL FIELD

The present invention relates to a blood analysis apparatus for measuring glucose and glycohemoglobin (HbAlc) contained in a blood sample.

BACKGROUND ART

Glucose and glycohemoglobin in blood are measured to perform a screening test and treatment of diabetes.

A method of measuring the glucose in the blood includes a method called an electrode method. This method is a method of outputting information correlated to a glucose concentration in a blood sample to an electrode brought into contact with the blood sample, and calculating the glucose concentration based on such output (see e.g., Patent Documents 1 and 2). The electrode method can be roughly classified into an equilibrium point method (end point method) and a differentiation method (rate method) depending on a calculation technique thereof. The equilibrium point method is a method of calculating the glucose concentration based on an equilibrium value of when a temporal change of the output from the electrode asymptotically approaches a constant value. On the other hand, the differentiation method is a method of calculating the glucose concentration based on a maximum value of when the output is differentiated n times (n is a positive integer). The electrode method also includes a method of associating a calculation result in the equilibrium point method and a calculation result in the differentiation method.

A liquid chromatography method is widely used for the method of measuring the glycohemoglobin (see e.g., Patent Documents 3 and 4). In this method, the glycohemoglobin is calculated as a proportion the glycohemoglobin occupies in a hemoglobin content based on a chromatogram indicating a relationship between elution time and elution amount (e.g., optical information such as absorbance).

At clinical sites, both the glucose and the glycohemoglobin are measured to treat the diabetes. Thus, an analysis apparatus and an analyzing system capable of measuring both the glucose and the glycohemoglobin are being developed and sold.

An analysis apparatus for measuring both the glucose and the glycohemoglobin includes an analysis apparatus in which a mechanism for measuring the glucose and a mechanism for measuring the glycohemoglobin are integrated in one device ("DM-JACK": manufactured by Kyowa Medex Co., Ltd.). This analysis apparatus adopts an enzyme method, which is a biochemical method, for the glucose measurement method and an immunization method for the glycohemoglobin measurement method.

Figure 11:
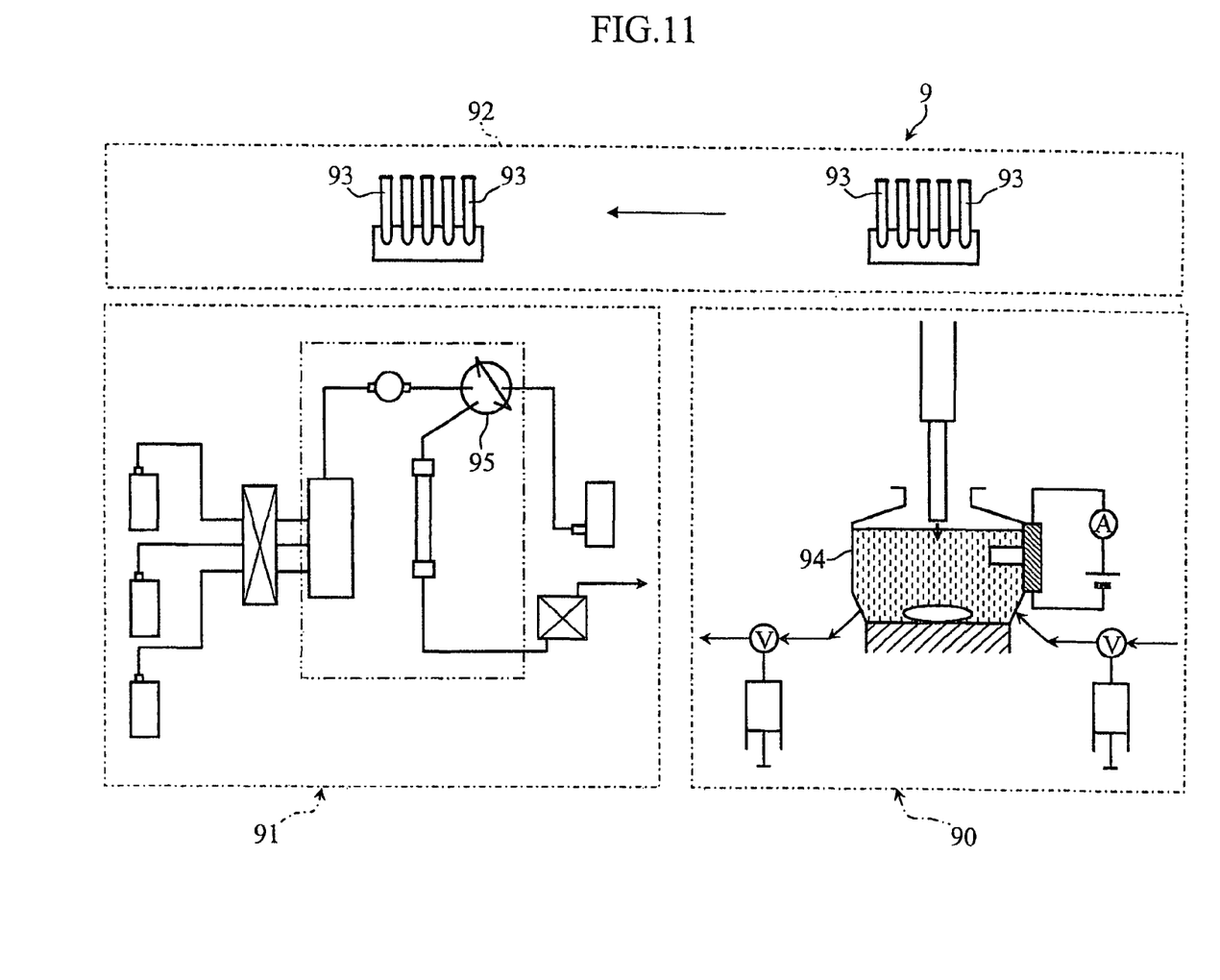
FIG. 11 is a schematic configuration view showing one example of a conventional analyzing system.

As shown in FIG. 11, an analyzing system 9 for measuring both the glucose and the glycohemoglobin includes an analyzing system in which a glucose measurement device 90 and a glycohemoglobin measurement device 91 are coupled for use ("HA70/GA70 simple conveying system": manufactured by ARKRAY Inc., system combining "HLC723 G8" (manufactured by Tosoh Corporation) and "GA08" (manufactured by A&T Corporation)).

Such a system 9 uses a device for measuring the glucose through the electrode method for the glucose measurement device 90, and a device for measuring the glycohemoglobin through the HPLC method for the glycohemoglobin measurement device 91. The analyzing system 9 couples the glucose measurement device 90 and the glycohemoglobin measurement device 91, and commonly uses one specimen conveying mechanism 92 in the devices 90 and 91. The specimen conveying mechanism 92 is configured to move a blood collecting tube 93 from a position where a specimen can be collected from the blood collecting tube 93 in the glucose measurement device 90 to a position where a specimen can be collected from the blood collecting tube 93 in the glycohemoglobin measurement device 91. In other words, the analyzing system 9 is configured such that the specimen collected from the blood collecting tube 93 in the glucose measurement device 90 is introduced into a reaction bath 94 to measure the glucose concentration, while the specimen collected from the blood collecting tube 93 in the glycohemoglobin measurement device 91 is introduced into an injection valve 95 to measure the glycohemoglobin.

However, the conventional analysis apparatus and the analyzing system 9 perform sampling of the specimen and preparation of the sample for measuring the glucose concentration, and the sampling of the specimen and the preparation of the sample for measuring the glycohemoglobin concentration independently. In other words, although the concentrations of both the glucose and the glycohemoglobin can be measured in the conventional analysis apparatus and the analyzing system 9, the sampling of the specimen and the preparation of the sample each need to be carried out twice to measure the concentration of the respective components. Thus, in the conventional analysis apparatus and the analyzing system 9, a configuration of the device or the system becomes complicated and a size of the device or the system is enlarged. In particular, since the analyzing system 9 is obtained by simply coupling two existing devices 90 and 91, a user is imposed with the same load as when using two devices. That is, the glucose measurement device 90 and the glycohemoglobin measurement device 91 need to be operated independently to measure the glucose concentration and the glycohemoglobin concentration, and the devices 90 and 91 need maintenance to be performed independently. In addition, as a portion related to measurement is not commonly shared at all in the two devices 90 and 91, an installation area for two devices is necessary, and a cost of the specimen conveying mechanism 92 is necessary in addition to a cost for the two devices.

Furthermore, in the above-described analysis apparatus, measurement accuracy of the glycohemoglobin concentration is not satisfactory since the immunization method is adopted for the measurement method of the glycohemoglobin concentration.

[Patent Document 1] Japanese Unexamined Patent Publication No. 9-33533
[Patent Document 2] Japanese Unexamined Patent Publication No. 2005-148058
[Patent Document 3] Japanese Unexamined Patent Publication No. 5-5730
[Patent Document 4] Japanese Unexamined Patent Publication No. 9-178719

DISCLOSURE OF THE INVENTION

Problems to be Solved by the Invention

The present invention aims to cost effectively provide a blood analysis apparatus capable of measuring concentrations of both glucose and glycohemoglobin at satisfactory accuracy without enlarging the device.

The present invention further aims to provide a blood analysis apparatus capable of alleviating an operation/maintenance load of the user.

Means for Solving the Problems

The present invention provides a blood analysis apparatus for measuring glucose and glycohemoglobin in blood, in which measurement of the glucose and the glycohemoglobin is carried out by one sampling of a blood sample.

The blood analysis apparatus according to the present invention is configured, for example, such that preparation of a measurement sample for measuring the glucose and preparation of a measurement sample for measuring the glycohemoglobin are simultaneously carried out by one sample preparation.

The measurement sample is prepared, for example, by diluting the blood sample using a diluent. Dilution of the blood sample for measuring the glycohemoglobin and dilution of the blood sample for measuring the glucose are carried out using an identical diluent.

The diluent used in the present invention may also be used as a cleaning fluid of a flow path through which the measurement sample moves. A diluent containing supporting electrolyte, for example, is used, and the diluent preferably has a buffering ability. The diluent may contain an antiseptic and Na azide is preferably used for the antiseptic.

A blood sample containing blood cells, for example, is preferably used. In this case, the diluent containing a surface acting agent for hemolyzing the blood cells is used.

The blood analysis apparatus according to the present invention preferably includes a stirring function of completely or almost completely hemolyzing the blood cells when diluting the blood sample, and may also include a function of stirring the blood sample for making blood cell concentration in the blood sample uniform.

The blood analysis apparatus according to the present invention is configured to perform measurement of the glucose using an enzyme electrode method. Such a blood analysis apparatus includes a sampling mechanism for sampling a blood sample from a sample container; a dilution bath for diluting the blood sample; a sample injection valve for introducing a measurement sample prepared in the dilution bath to a glycohemoglobin measurement mechanism for measurement of the glycohemoglobin; a pipe for connecting the sample injection valve and the dilution bath; a sample introducing pump for introducing the measurement sample from the dilution bath to the sample injection valve; and an enzyme electrode for measurement of the glucose.

The blood analysis apparatus according to the present invention may further include a temperature adjustment unit for simultaneously controlling temperatures of the enzyme electrode and a device for measuring the glycohemoglobin (e.g., column for liquid chromatography).

The enzyme electrode is preferably arranged on or in a middle of the pipe. The enzyme electrode may also be arranged in the dilution bath, or may be arranged in the sample injection valve.

The blood analysis apparatus according to the present invention is configured, for example, such that the glycohemoglobin is measured using a liquid chromatography method.

The blood analysis apparatus according to the present invention is preferably configured to simultaneously measure hemoglobin concentration of the whole blood sample and correct a glucose whole blood measurement result to a plasma conversion value using the hemoglobin concentration when whole blood sample is used for the blood sample. The hemoglobin concentration is obtained based on a chromatogram obtained in measurement of the glycohemoglobin.

The blood analysis apparatus of the present invention may be configured to simultaneously output the measurement result of the glucose and the measurement result of the glycohemoglobin for every patient. As used herein, "output" includes displaying on a display device of the blood analysis apparatus, printing on a printing medium such as recording paper, and recording on a recording medium (flexible disc, optical recording medium, IC memory, or the like).

The blood analysis apparatus according to the present invention is preferably configured to measure the glucose first, and then measure the glycohemoglobin. In this case, the blood analysis apparatus according to the present invention is preferably configured to carry out determination on whether to perform or cancel the measurement of the glycohemoglobin based on a measurement result of the glucose. The determination on whether to perform or cancel the measurement of the glycohemoglobin is made based on a disease type classification flowchart in diagnosis of diabetes. In addition, a determination result of the disease classification of the diabetes may be simultaneously output with a measurement result of the glucose and a measurement result of the glycohemoglobin.

DESCRIPTION OF THE REFERENCE SYMBOLS

X: Blood analysis apparatus
50: Nozzle (of sampling mechanism)
51: Dilution bath
52: Pump (of sampling mechanism)
6: Injection valve
7: Glycohemoglobin measurement mechanism
81: Sensor unit (enzyme electrode)

BEST MODE FOR CARRYING OUT THE INVENTION

Hereinafter, specific examples of the present invention will be described with reference to FIGS. 1 to 8.

Figure 1:
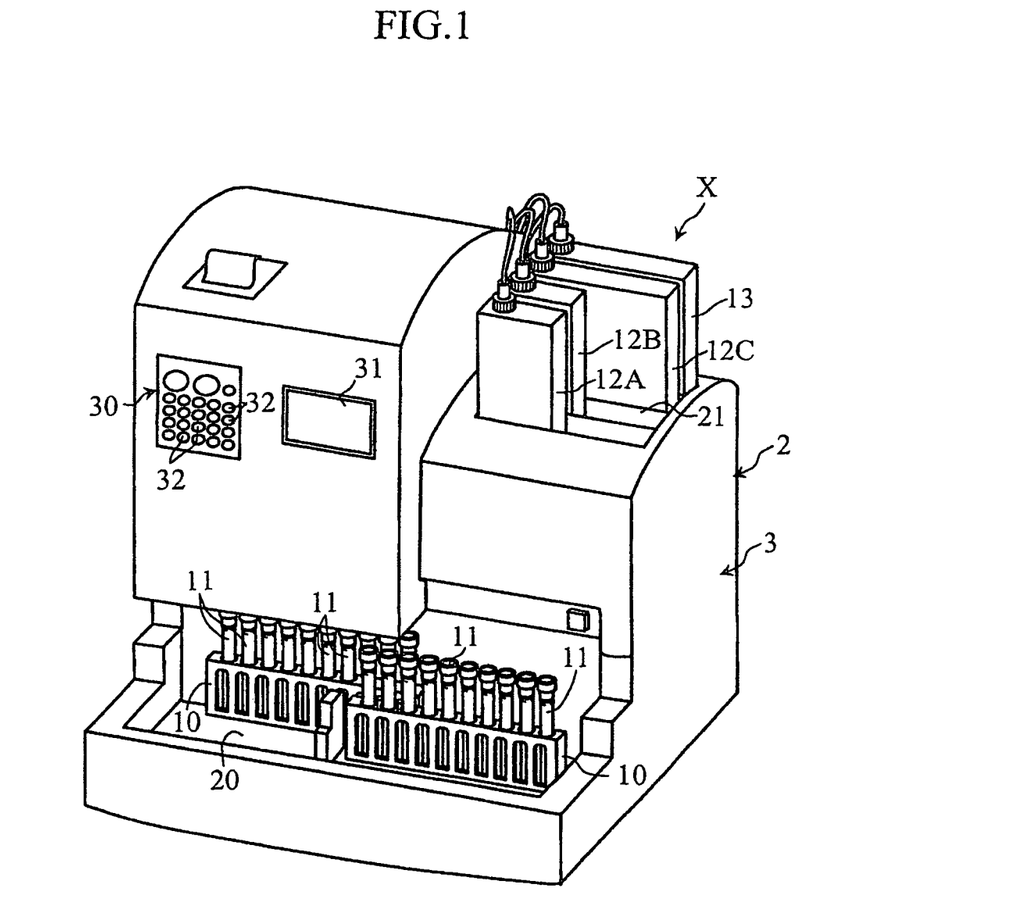
FIG. 1 is a general perspective view showing one example of a blood analysis apparatus according to the present invention.

A blood analysis apparatus X shown in FIG. 1 is configured to automatically measure glucose and glycohemoglobin in whole blood by setting a blood collecting tube 11 held in a rack 10 on a table 20. The blood analysis apparatus X includes a plurality of eluent bottles 12A, 12B, and 12C (three in the figure), a hemolysis cleaning fluid bottle 13, and a device main body 2.

Each of the eluent bottles 12A, 12B, and 12C holds an eluent to supply to an analysis column 70 (see FIG. 2) described below, and is arranged in a holder 21 of the device main body 2. A buffer having a different pH and a salt concentration, and the like is used for the eluent.

The hemolysis cleaning fluid bottle 13 holds a hemolysis cleaning fluid. This hemolysis cleaning fluid bottle is also arranged in the holder 21 of the device main body 2. The hemolysis cleaning fluid has both an ability to hemolyze the blood cells in the whole blood and dilute a target component, and an ability to clean pipes. The hemolysis cleaning fluid containing, for example, a buffering agent, a hemolyzing agent, and a supporting electrolyte is used.

The buffering agent maintains the hemolysis cleaning fluid at a range of the target pH. The buffering agent merely needs to exhibit a buffering action in the target pH range, and phosphate such as potassium phosphate may be used if the hemolysis cleaning fluid has a buffering ability in a neutral region. A concentration of the buffering agent in the hemolysis cleaning fluid is set to be between 0.0001 and 0.1 M.

The hemolyzing agent breaks a blood cell film of a blood cell component in the blood. For the hemolyzing agent, various known hemolyzing agents such as ammonium chloride may be used in addition to surface acting agents such as polyoxyethylene(10)octylphenyl ether (TritonX-100), higher fatty acid alcohol, alkyl aryl polyether alcohol, polyoxyethylene glycol of sulphonate, polyoxyethylene ether of sulfate, and a polyoxyethylene derivative of dehydrated sorbitan fatty acid ester. The concentration of the hemolyzing agent in the hemolysis cleaning fluid is set, for example, between 0.01 and 1.0 vol %.

The supporting electrolyte stabilizes an ion strength in the hemolysis cleaning fluid. Salt of alkali metal or alkaline earth metal can be used for the supporting electrolyte, and among them, Na salt such as NaCl and K salt such as KCl are preferably used. The concentration of the supporting electrolyte in the hemolysis cleaning fluid is set, for example, between 0.01 and 0.4 M.

The hemolysis cleaning fluid may contain an antiseptic such as 2-phenoxyetanol or Na azide. If Na azide is used for the antiseptic, an Hb influence on a glucose reaction can be reduced.

Figure 2:
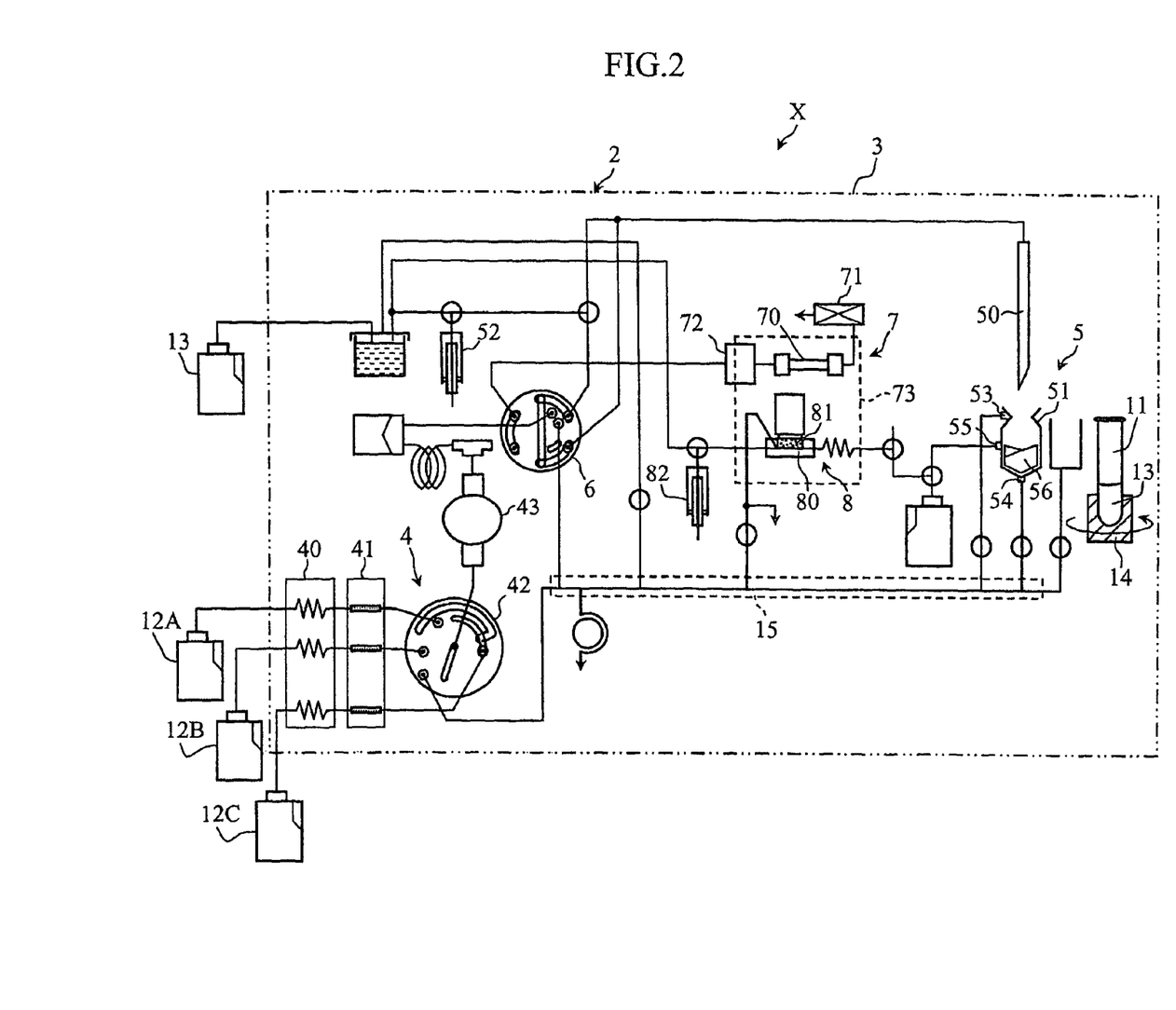
FIG. 2 is a schematic configuration view of the blood analysis apparatus shown in FIG. 1.

In addition to the table 20 and the holder 21, the device main body 2 includes a liquid supply mechanism 4, a sample preparation mechanism 5, an injection valve 6, a glycohemoglobin measurement mechanism 7, and a glucose measurement mechanism 8 accommodated inside a housing 3, as shown in FIG. 2.

As shown in FIG. 1, the table 20 is configured to move the blood collecting tube 11 held at the rack 10 to a position where it can be collected by a nozzle 50 in the sample preparation mechanism 5 described below, by moving the rack 10 set at a predetermined site. As shown in FIG. 2, blood 13 of the blood collecting tube 11 can be stirred by a stirring mechanism 14 in the blood analysis apparatus X.

The stirring mechanism 14 may adopt a configuration of rotating the blood collecting tube 11 in a peripheral direction. It should be recognized that the stirring mechanism 14 may adopt other configurations such as a configuration of stirring the blood 13 of the blood collecting tube 11 by applying vibration to the blood collecting tube 11, and a configuration of stirring the blood 13 of the blood collecting tube 11 by rotating a rotor arranged inside the blood collecting tube 11.

In the blood analysis apparatus X of FIG. 1, a plurality of blood collecting tubes 11 is held at one rack 10, but one blood collecting tube 11 may be set at a target position of the device main body 2 without using the rack 10.

Figure 3:
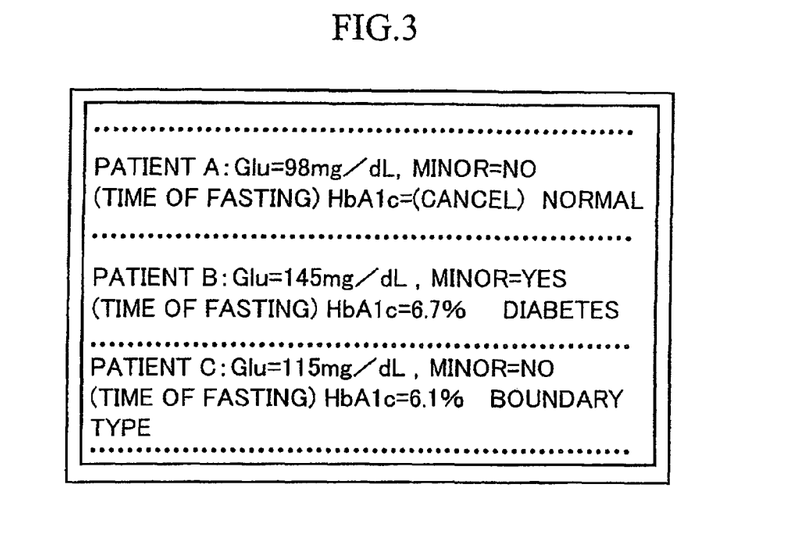
FIG. 3 is a view showing one example of a measurement result displayed on a display panel in the blood analysis apparatus shown in FIG. 1.
Figure 4:
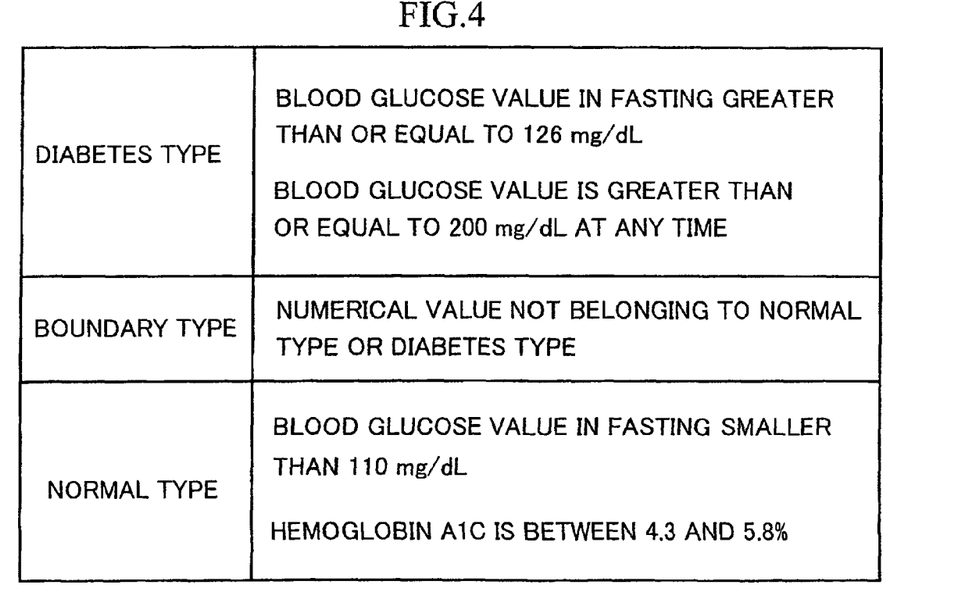
FIG. 4 is a view showing one example of a disease type classification flowchart of diabetes.

The housing 3 defines an outer shape of the device, and has an operation panel 30 and a display panel 31 arranged on a surface thereof. The operation panel 30 is provided with a plurality of operation buttons 32, where a signal for performing various operations (analysis operation, printing operation, and the like) can be generated or various settings (setting of analysis condition, LD input of the subject, and the like) can be performed by operating the operation button 32. The display panel 31 displays an analysis result or an error, and displays an operation procedure at the time of setup, an operation state, and the like. The analysis result displayed on the display panel 31 also includes disease type classification classified by a diabetes diagnosis (disease type classification) flowchart shown in FIG. 4, in addition to the measurement results of the glucose and the glycohemoglobin, as shown in FIG. 3.

As shown in FIG. 2, the liquid supply mechanism 4 supplies the eluent of the plurality of eluent bottles 12A, 12B, and 12C individually to the injection valve 6. The liquid supply mechanism 4 includes a temperature adjustment unit 40, a deaeration unit 41, a switching valve 42, and a liquid feeding pump 43.

The temperature adjustment unit 40 adjusts the eluent to a target temperature before supplying the eluent to the analysis column 70 described below. The temperature adjustment unit 40 is configured to adjust temperatures of the plurality of eluent bottles 12A, 12B, and 12C individually. Such a temperature adjustment unit 40 can be achieved by a heating means provided on the flow path of each eluent. The temperature adjustment unit 40 may control the temperature of each eluent by detecting the temperature of each eluent, and controlling the heating means according to the detected temperature.

The deaeration unit 41 removes dissolved gas from the eluent before supplying the eluent to the analysis column 70 described below. The deaeration unit 41 may be configured by having a middle of the flow path of each eluent formed by a hollow gas-liquid separation film, and the gas-liquid separation film arranged in a chamber. In such a configuration, the dissolved gas can be removed from the eluent flowing through the gas-liquid separation film by depressurizing the chamber. It should be recognized that the deaeration unit 41 may have a configuration other than the configuration of depressurizing the chamber accommodating the gas-liquid separation film.

The switching valve 42 selects the type (eluent bottle 12A, 12B, 12C) of eluent to supply to the injection valve 6. The switching operation of the switching valve 42 is controlled by a control means (not shown).

The liquid feeding pump 43 supplies the eluent of the eluent bottles 12A, 12B, and 12C to the injection valve 6 and the analysis column 70 described below. Various known types of liquid feeding pump can be used for the liquid feeding pump 43.

The sample preparation mechanism 5 prepares the measurement sample to introduce to the glycohemoglobin measurement mechanism 6 and the glucose measurement mechanism 7 based on the blood 13 collected from the blood collecting tube 11. The sample preparation unit 5 includes a nozzle 50, a dilution bath 51, and a pump 52.

The nozzle 50 collects the blood 13 of the blood collecting tube 11, and supplies the measurement sample of the dilution bath 51 to the injection valve 6. The nozzle 50 can aspirate and discharge the blood 13 and the measurement sample by power of the pump 52, and can be moved in a vertical direction and a horizontal direction. The operation of the nozzle 50 is controlled by the control means (not shown).

Figure 5:
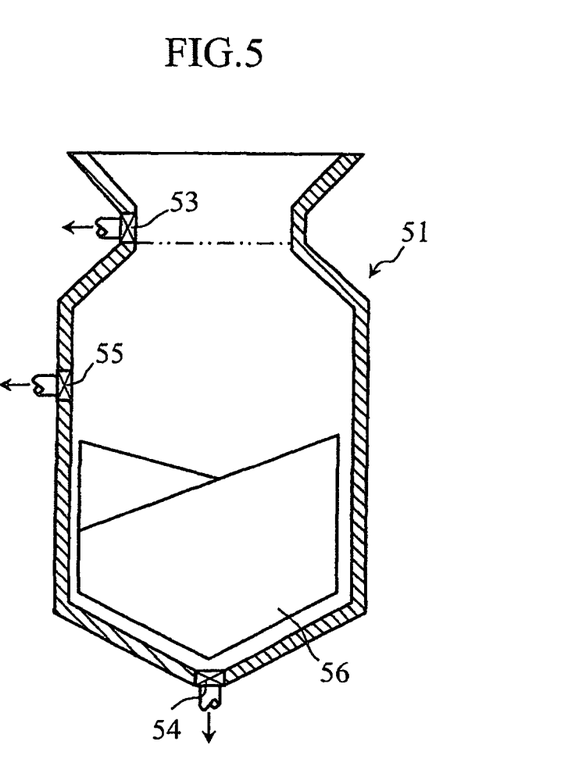
FIG. 5 is a cross-sectional view describing a dilution bath in the blood analysis apparatus shown in FIG. 1.

As shown in FIGS. 2 and 5, the dilution bath 51 hemolyzes red blood cells in the blood 13, and provides a place to dilute the hemolyzed blood and prepare the measurement sample. The dilution bath 51 is connected to a drain system 15 by way of open/close valves 53 and 54 at an upper part and a bottom part, and is connected to a light measurement cell 80 of a glucose measurement mechanism 8 described below, by way of an open/close valve 55 at a central part. The elution cleaning liquid flows out from the dilution bath 51 through the open valve 53 at the upper part when a great amount of hemolysis cleaning fluid more than necessary is supplied to the dilution bath 51 by closing the open valve 54 at the bottom part and opening the open valve 53 at the upper part. With this configuration, the dilution bath 51 can hold the liquid of a constant amount. The liquid of the dilution bath 51 can be discharged to the drain system 15 by opening the open valve 53 at the bottom part. The hemolysis cleaning fluid of the dilution bath 51 can be supplied to the light measurement cell 80 of the glucose measurement mechanism 8 by opening the open valve 55.

A rotor 56 is further accommodated inside the dilution bath 51. A rotation state of the rotor 56 is controlled by the control means (not shown), where the liquid of the dilution bath 51 can be stirred by rotating the rotor 56. It should be recognized that a design of configuration for rotating the liquid of the dilution bath 51 can be changed.

As shown in FIG. 2, the pump 52 applies an aspiration force or a discharge force to an interior of the nozzle 50. Various known types of pumps can be used for the pump 52.

The injection valve 6 quantifies the sample of a constant amount (e.g., a few microliters) to be introduced to the analysis column 70 and introduces such a sample to the analysis column 70, and is communicable to the switching valve 42, the nozzle 50, the analysis column 70 described below, and the drain system 15. The communication state in the injection valve 6 is controlled by the control means (not shown).

The glycohemoglobin measurement mechanism 7 measures the glycohemoglobin concentration in the blood using a liquid chromatography method, and includes the analysis column 70 and the light measurement unit 71.

The analysis column 70 is filled with a filler, and is connected to the injection valve 6 by way of a pre-filter 72. The analysis column 70 is maintained at a target temperature such as a temperature of about 40° C. by the temperature adjustment mechanism 73. In measuring the concentration of the glycohemoglobin, methacrylic acid ester copolymer and the like is used for the filler. Various known types of temperature adjustment mechanism can be used for the temperature adjustment mechanism 73, but a mechanism of arranging the analysis column 70 in the chamber and adjusting the temperature of the chamber by a heating heater is adopted.

Figure 6:
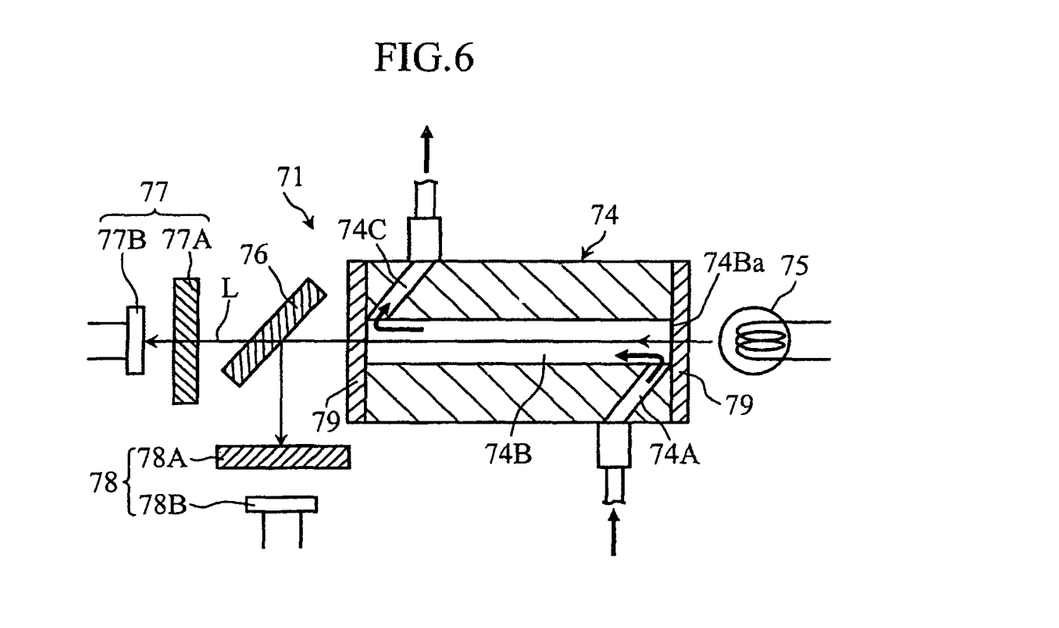
FIG. 6 is a cross-sectional view describing a light measurement unit in an HPLC device shown in FIG. 1.

The light measurement unit 71 optically detects the hemoglobin contained in the eluent from the analysis column 70, and includes a light measurement cell 74, a light source 75, a beam splitter 76, a measurement light receiving system 77, and a reference light receiving system 78, as shown in FIG. 6.

The light measurement cell 74 defines a light measuring area. The light measurement cell 74 includes an introduction flow path 74A, a light measurement flow path 74B, and a discharge flow path 74C, which flow paths 74A, 74B, and 74C are communicated in series. The introduction flow path 74A introduces the eluent from the analysis column 70 (see FIG. 2) to the light measurement flow path 74B. The light measurement flow path 74B flows the eluent from the analysis column 70 (see FIG. 2) to be light measured and provides a place for light measuring the eluent, and is formed in a straight line. The light measurement flow path 74B is opened at both ends, where the both ends are blocked by a transparent cover 79. The discharge flow path 74C discharges the eluent of the light measurement flow path 74B.

The light source 75 applies light on the eluent flowing through the light measurement flow path 74B. The light source 75 is arranged facing an end face 74Ba (transparent cover 79) of the light measurement flow path 74B such that an optical axis L passes the center of the light measurement flow path 74B. The light source 75 that can emit light of a wavelength range including light of 415 to 430 nm, which is a maximum absorption wavelength of oxyhemoglobin, and 500 nm, which is a reference wavelength, such as a halogen lamp may be used. It should be recognized that the light source 75 equipped with one or more LED elements may be used other than the halogen lamp.

The beam splitter 76 divides the light transmitted through the light measurement flow path 74B of the light emitted from the light source 75 so that the light enters to the measurement light receiving system 77 and the reference light receiving system 78, and is arranged on the optical axis L in a state inclined by 45 degrees. Various known types of beam splitter such as a half mirror can be used for the beam splitter 76.

The measurement light receiving system 77 arranged on the optical axis L selectively receives the light of 415 to 430 nm, which is the maximum absorption wavelength of the oxyhemoglobin, of the light transmitted through the beam splitter 76. The measurement light receiving system 77 includes an interference filter 77A for selectively transmitting the light of 415 to 430 nm, and a light receiving element 77B for receiving the light transmitted through the interference filter 77A. A photodiode may be used for the light receiving element 77B.

The reference light receiving system 78 selectively receives the light of 500 nm, which is the reference wavelength, of the light reflected at the beam splitter 76 and the optical path is changed. The measurement light receiving system 78 includes an interference filter 78A for selectively transmitting the light of 500 nm, and a light receiving element 78B for receiving the light transmitted through the interference filter 78A. A photodiode may be used for the light receiving element 78B.

Figure 8:
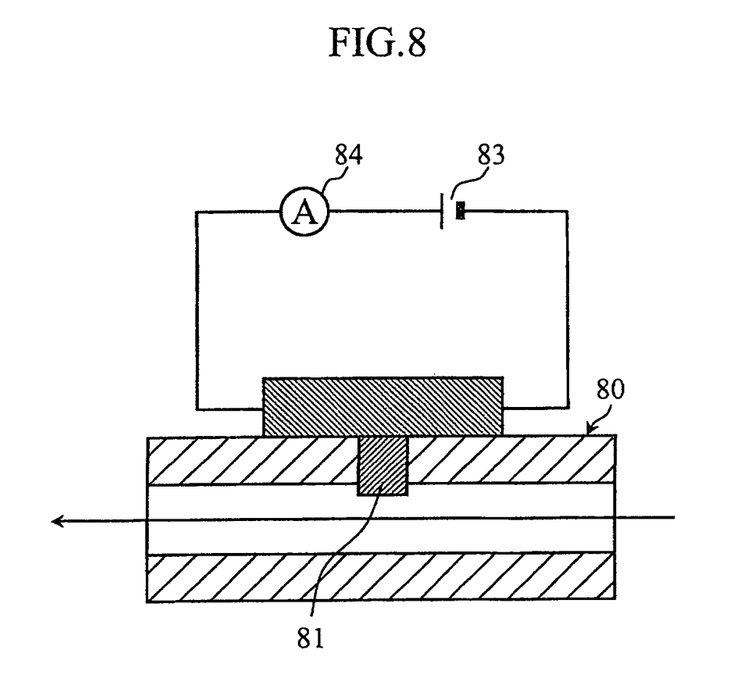
FIG. 8 is a cross-sectional view describing a glucose measurement mechanism in the blood analysis apparatus shown in FIG. 1.

As shown in FIGS. 2 and 8, the glucose measurement mechanism 8 measures the glucose in the blood. The glucose measurement mechanism 8 includes a measurement cell 80, a sensor unit 81, a pump 82, a power supply 83, and a current value measurement unit 84, where at least the light measurement cell 80 and the sensor unit 81 are adjusted to the same temperature as the analysis column 70 by the same temperature adjustment mechanism 73 as the analysis column 70.

The measurement cell 80 provides a place for allowing the glucose contained in the measurement sample supplied from the dilution bath 51 to contact with the sensor unit 81.

The sensor unit 81 outputs an electrical physical quantity corresponding to an electron exchange quantity with the glucose in the measurement sample, and is configured so as to be repeatedly used. The sensor unit 81 includes an enzyme immobilization layer and an electrode, for example, which are not shown in the figure. The enzyme immobilization layer is configured to include, for example, glucose oxidase (GOD) or glucose dehydrogenase (GDH). The configuration of the electrode is selected according to the type of enzyme contained in the enzyme immobilization layer. For example, when using GOD for the enzyme, a hydrogen peroxide electrode is used for the electrode.

The pump 82 supplies the measurement sample of the dilution bath 51 to the light measurement cell 80. Various known types of pump can be used for the pump 82, and a supply speed of the measurement sample with respect to the light measurement cell 80 is, for example, between 1.6 and 1.8 mL/min.

The power supply 83 applies voltage to the electrode of the sensor unit 81. ADC (direct-current) power supply is used for the power supply 83, and the applied voltage on the electrode is set to, for example, between 0.64 and 0.66 V.

The current value measurement unit 84 measures the electron exchange quantity between the electrode of the sensor unit 81 and the glucose as a current value. Here, assuming a case where GOD is used for the enzyme and a hydrogen peroxide electrode is used for the electrode, the glucose is broken down to gluconic acid and hydrogen peroxide by the action of the GOD in the enzyme immobilization layer of the sensor unit 81. The hydrogen peroxide is reduced by the application of voltage on the electrode of the sensor unit 81 and broken down to oxygen and hydrogen ions by providing electron to an anode. In this case, a current flows between the anode and a cathode by the electron provided to the anode, and the current at the time is measured in the current value measurement unit 84.

Next, an operation of a blood analysis apparatus X will be described.

When measuring the glucose and the glycohemoglobin using the blood analysis apparatus X, the rack 10 is first set at a predetermined site of the table 20 with the blood collecting tube 11 containing the blood 13 held in the rack 10.

In the blood analysis apparatus X, the rack 10 is moved at the table 20 and the measurement sample is prepared based on the blood 13 of the target blood collecting tube 11 when an instruction to start the measurement is confirmed. The instruction to start the measurement is made by the user by operating a predetermined operation button 32 of the blood analysis apparatus X.

The measurement sample is prepared by supplying the hemolysis cleaning fluid and the blood 13 to the dilution bath 51, and stirring and mixing the same.

In supplying the hemolysis cleaning fluid to the dilution bath 51, first the interior of the nozzle 50 of the sample preparation mechanism 5 and the hemolysis cleaning fluid bottle 13 are communicated, the open/close valve 53 in the dilution bath 51 is opened, and the open/close valves 54 and 55 are closed. In this state, the nozzle 50 is moved to a position corresponded to the dilution bath 51. Next, the hemolysis cleaning fluid of the hemolysis cleaning fluid bottle 13 is supplied to the dilution bath 51 via the nozzle 50 using the power of the pump 52. In this case, the excessively supplied hemolysis cleaning fluid is discarded to the drain system 15 via the open/close valve 53 since the open/close valve 53 is in an opened state. As a result, a constant amount of hemolysis cleaning fluid is reliably supplied to the dilution bath 51. The amount of hemolysis cleaning fluid to supply to the dilution bath 51 is, for example, between 1.3 and 1.7 ml.

On the other hand, the blood sample is supplied by aspirating the blood sample into the nozzle 50, and then discharging the blood sample in the nozzle 50 to the dilution bath 51. The blood sample is aspirated to the nozzle 50 by applying the aspiration force to the interior of the nozzle 50 by the pump 52 with a distal end of the nozzle 50 immersed in the blood sample. In this case, the blood 13 of the blood collecting tube 11 is stirred by the stirring mechanism 14. Thus, in the blood collecting tube 11, the blood cell component in the blood 13 is evenly dispersed. As a result, the blood 13 collected by the nozzle 50 appropriately reflects the blood cell concentration of the blood 13 at the time of blood collection. An aspiration amount of the blood sample by the nozzle 50 is, for example, between 20 and 40 μL. The blood 13 is supplied to the dilution bath 51 by moving the nozzle 50 to the position corresponding to the dilution bath 51, and applying the discharge force to the interior of the nozzle 50 by means of the pump 52.

The hemolysis cleaning fluid and the blood 13 supplied to the dilution bath 51 are mixed by rotating the rotor 56 of the dilution bath 51 with the open/close valves 53, 54, and 55 closed. The blood 13 contains the blood cell component, while the hemolysis cleaning fluid contains the hemolyzing agent. Thus, when the blood 13 and the hemolysis cleaning fluid coexist in the dilution bath 51, the blood cells are hemolyzed, and a component within the blood cell is eluted in the hemolysis cleaning fluid. Since the blood cell components are evenly dispersed in the hemolysis cleaning fluid by rotating the rotor 56 in the dilution bath 51, the blood cell components can be reliably hemolyzed in a short period of time, and the component within the blood cell can be evenly dispersed in the hemolysis cleaning fluid.

The blood analysis apparatus X performs the measurement of the glucose in the glucose measurement mechanism 8 when completion of the preparation of the sample in the dilution bath 51 is confirmed. More specifically, the open valve 55 of the dilution bath 51 is opened, and the sample of the dilution bath 51 is supplied to the measurement cell 80 by the power of the pump 82. In the measurement cell 80, the enzyme immobilization layer (not shown) of the sensor unit 81 is brought into contact with the measurement sample, and thus the electrons are supplied from the glucose contained in the measurement sample to the enzyme immobilization layer, and these electrons are supplied to the electrode (not shown) of the sensor unit 81. The voltage is applied to the sensor unit 81 by the power supply 83, and the current corresponding to an electron supply amount with respect to the sensor unit 81 (electrode) is measured by the current value measurement unit 84.

In the blood analysis apparatus X, the glucose concentration is further calculated based on the current value measured in the current value measurement unit 84. The calculation of the glucose concentration is performed through a known method such as an equilibrium point method (end point method), a differentiation method (rate method), or a combination thereof.

The blood glucose measurement device X determines whether or not the glucose concentration is in a normal range. This determination is made based on the disease type classification flowchart in the diagnosis of diabetes shown in FIG. 4. More specifically, the blood analysis apparatus X determines whether or not the glucose concentration is less than 110 mg/dL if the blood 13 is from the time of fasting, and whether or not the glucose concentration is less than 200 mg/dL if the blood 13 is not from the time of fasting. The blood analysis apparatus X determines not to perform the measurement of the glycohemoglobin if it determines that the glucose concentration is less than 110 mg/dL at the time of fasting or the glucose concentration is less than 200 mg/dL at the time of nonfasting (at an ordinary time) since the blood glucose value is in the normal range. The blood analysis apparatus X performs the measurement of the glycohemoglobin if it determines that the glucose concentration is greater than or equal to 110 mg/dL at the time of fasting or the glucose concentration is greater than or equal to 200 mg/dL at the time of nonfasting (at an ordinary time).

The measurement of the glycohemoglobin in the blood analysis apparatus X is carried out by the glycohemoglobin measurement mechanism 7. More specifically, the eluent is supplied to the injection valve 6. The eluent is supplied from the eluent bottles 12A, 12B, and 12C to the injection valve 6 through the temperature adjustment unit 40, the deaeration unit 41, and the switching valve 42 by the power of the liquid feeding pump 43, and which eluent of the eluent bottles 12A, 12B, and 12C is to be supplied out of the plurality of eluent bottles 12A, 12B, and 12C is selected by controlling the switching valve 42. In the blood analysis apparatus X, since the eluent is supplied to the injection valve 6 through the temperature adjustment unit 40 and the deaeration unit 41, the eluent supplied to the injection valve 6 is maintained at a target temperature and removed with dissolved gas.

The eluent supplied to the injection valve 6 is supplied to the analysis column 70 through the pre-filter 72 by switching the injection valve 6. The analysis column 70 is thereby equilibrated.

The measurement sample of the dilution bath 51 is introduced to the injection valve 6. The measurement sample of the dilution bath 51 is introduced to the injection valve 6 using the power of the pump 52 with the nozzle 50 immersed in the dilution bath 51. In this case, the sample is quantified in the injection valve 6 since the measurement sample of a constant amount is held in the injection valve 6. The amount of measurement sample to be supplied to the injection valve 6 is, for example, between 2 and 6 µL.

Through the switching operation of the injection valve 6, the measurement sample of the injection valve 6 is introduced to the analysis column 70 with the eluent. If a constant period of time has elapsed from the start of introduction of the introducing sample, the eluent is continuously supplied to the analysis column 70 by performing the switching operation of the injection valve 63.

In the analysis column 70, hemoglobin including glycohemoglobin is adsorbed to the filler due to the introduction of the measurement sample. After the hemoglobin is adsorbed to the filler, the type of eluent to be supplied to the analysis column 70 is appropriately switched by the switching valve 42 to elute the hemoglobin adsorbed to the filler.

The eluent containing the glycohemoglobin discharged from the analysis column 70 is supplied to the light measurement cell 74. In the light measurement cell 74, the eluent is introduced through the introduction flow path 74A, and such an eluent is discarded through the discharge flow path 74C after passing through the light measurement flow path 74B.

In the light measurement unit 71, the light is continuously applied on the eluent by the light source 75 when the eluent passes through the light measurement flow path 74B. On the other hand, the light transmitted through the light measurement flow path 70B is received by the measurement light receiving system 77 and the reference light receiving system 78 after being divided by the beam splitter 76. In the measurement light receiving system 77, the light of between 415 and 430 nm, which is the maximum absorption wavelength of the oxyhemoglobin, transmitted through the interference filter 77A is selectively received at the light receiving element 77B. In the reference light receiving system 78, the light of 500 nm, which is the reference wavelength, transmitted through the interference filter 78A is selectively received at the light receiving element 78B.

Figure 7:
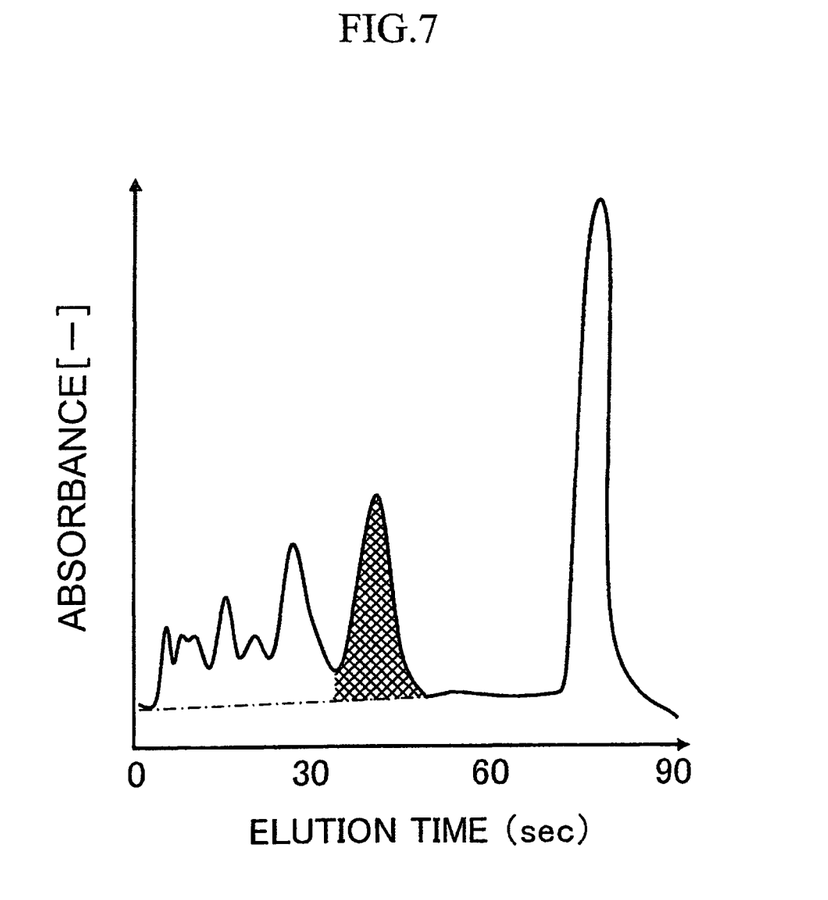
FIG. 7 is a graph showing one example of a chromatogram obtained in a glycohemoglobin measurement mechanism in the blood analysis apparatus shown in FIG. 1.

The light receiving results at the light receiving elements 77A and 78A are outputted to a calculation circuit (not shown). In such a calculation circuit, the chromatogram of the hemoglobin as shown in FIG. 7 is created based on the elution time and the light receiving amount. In the calculation circuit, the proportion of the glycohemoglobin (hemoglobin A1c) in the total amount of hemoglobin is also calculated. In this case, the calculation result of the glycohemoglobin may be corrected according to the calculation result of the hemoglobin obtained based on the chromatogram in the calculation circuit. In such a case, the calculation result of the glycohemoglobin obtained in the calculation circuit takes into consideration the blood cell component (hematocrit value) in the blood, and becomes similar to the proportion of the glycohemoglobin in the total amount of hemoglobin in a substantial blood plasma state.

Whether or not the calculation result of the glycohemoglobin is in the normal range is also determined in the calculation circuit. This determination is made based on the disease type classification flowchart in the diagnosis of diabetes shown in FIG. 4. More specifically, the calculation circuit determines whether or not the calculation result of the glycohemoglobin is in the range of between 4.3 and 5.8%. The calculation circuit determines as a boundary type if the calculation result of the glycohemoglobin is in the above range since the glucose concentration is high and the glycohemoglobin is in the normal range. The calculation circuit determines as diabetes if the glycohemoglobin is greater than the above range.

After the measurement of the glucose and the glycohemoglobin in the blood analysis apparatus X is terminated, the pipes and the dilution bath are cleaned for the next measurement. The hemolysis cleaning fluid of the hemolysis cleaning fluid bottle 13 is used in such a cleaning task.

In such a blood analysis apparatus X, the sample preparation is carried out by one sampling of the blood 13 to perform the measurement of the glucose and the glycohemoglobin. Thus, even when measuring two types of components, the sampling of the blood 13 can be performed in one nozzle 50, and only one pump 52 for applying the aspiration force and the discharge force on the nozzle 50 is required. The sample preparation may be simultaneously carried out on one dilution bath 51 to perform the measurement of the glucose and the glycohemoglobin. Thus, the sample can be prepared in one dilution bath 51 even when measuring two types of components. Therefore, in the blood analysis apparatus X, various elements are commonly used to measure the glucose and the glycohemoglobin, which is different from the conventional analyzing system 9 (see FIG. 11) and the analysis apparatus that perform the sampling of the blood 13 and the preparation of the measurement sample individually to measure the glucose and the glycohemoglobin. As a result, the configuration of the device or the system is simplified in the blood analysis apparatus X compared to the conventional analysis apparatus and the system 9 (see FIG. 11), whereby miniaturization of the device can be achieved and the installation area can be reduced. Similarly, since the glucose and the glycohemoglobin are measured in one device in the blood analysis apparatus X, a burden of maintenance is alleviated compared to the conventional analyzing system 9 (see FIG. 11) in which the glucose measurement device and the glycohemoglobin device are coupled.

In the blood analysis apparatus X, the operation on the measurement of two types of components can be carried out by operating the common operation panel 30 in measuring the glucose and the glycohemoglobin. Thus, a burden in measuring the glucose and the glycohemoglobin is alleviated in the blood analysis apparatus X.

The blood analysis apparatus X further has an advantage in that the measurement accuracy of the glycohemoglobin is high since the liquid chromatography method is adopted for the measurement method of the glycohemoglobin.

Furthermore, since the glycohemoglobin is measured according to the measurement result of the glucose in the blood analysis apparatus X, the measurement of the glycohemoglobin is not performed if it is apparent that the subject does not have diabetes, whereby the measurement time can be reduced when making the diagnosis of diabetes on a plurality of blood 13.

The present invention is not limited to the above embodiments, and various modifications may be made. For instance, the sensor unit (enzyme electrode) 81 is not limited to being arranged on or at the middle of the pipe connecting to the dilution bath, and may be arranged at other sites than the pipe, as illustrated in FIGS. 9 and 10.

Figure 9:
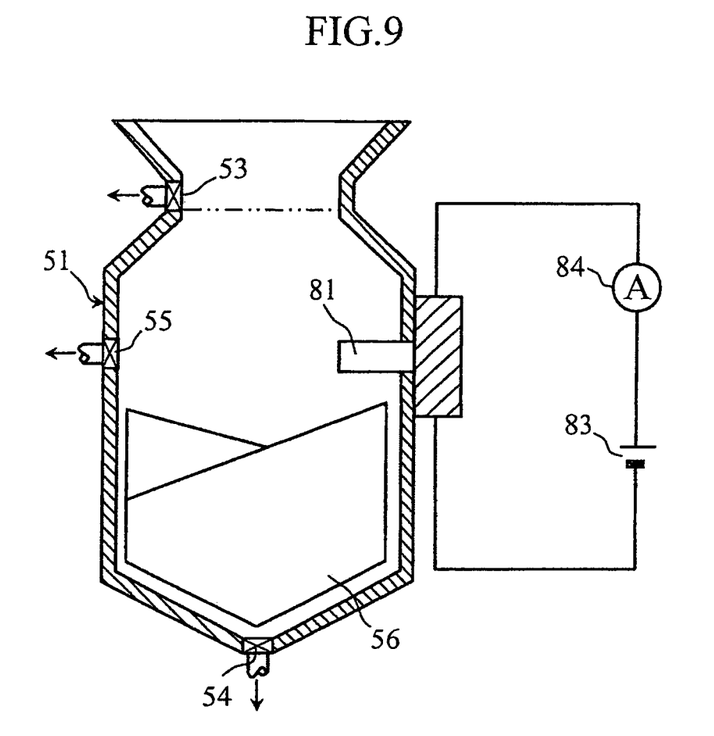
FIG. 9 is a cross-sectional view showing another example of the glucose measurement device.

The sensor unit 81 is arranged in the dilution bath 51 in the example shown in FIG. 9. The sensor unit 81 is fixed to a peripheral wall of the dilution bath 51, so that the enzyme immobilization layer (not shown) can be brought into contact with the liquid of the dilution bath 51. The sensor unit 81 is not limited to being fixed to the peripheral wall of the dilution bath 51 and may be fixed at other sites such as a bottom wall as long as it is at a position at which the sensor unit can be brought into contact with the liquid of the dilution bath 51.

Figure 10:
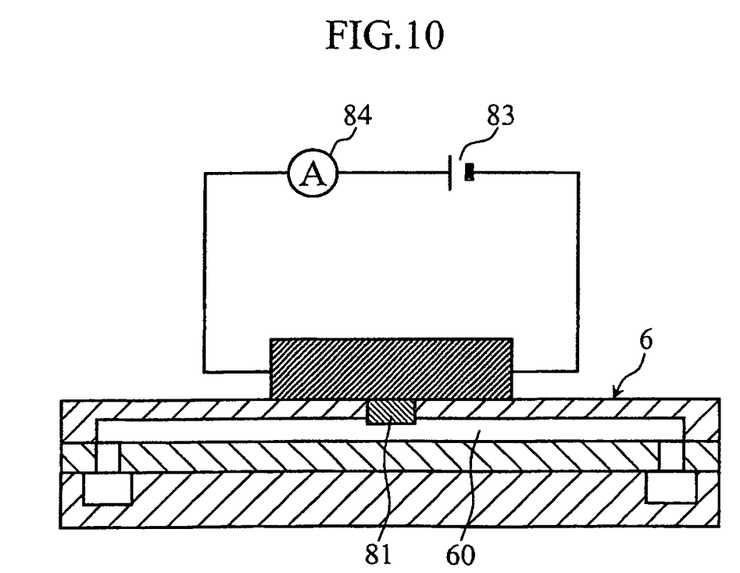
FIG. 10 is a cross-sectional view showing another further example of the glucose measurement device.

The sensor unit 81 is arranged in the injection valve 6 in the example shown in FIG. 10. The sensor unit 81 is fixed to a flow path 60 that enables communication of the dilution bath 51 with the analysis column 70, in the injection valve 6.

It should be recognized that the sensor unit may be arranged at other sites such as the pump 52 in addition to the injection valve 6 and the dilution bath 51 as long as it is at a position at which the sensor unit can be brought into contact with the measurement sample.

Whether or not to measure the glycohemoglobin is determined based on the measurement result of the glucose in the blood analysis apparatus X, but the glycohemoglobin may be measured irrespective of the measurement result of the glucose.

What is claimed is:

1. A blood analysis apparatus comprising:
a sampling unit configured to sample a blood sample by obtaining a specimen from the blood sample;
a preparation unit configured to dilute and prepare the specimen to produce as a measurement sample a first measurement sample for measuring a ratio of a content of glycohemoglobin to a content of hemoglobin in the specimen and a second measurement sample for measuring a concentration of glucose of the specimen;
a glycohemoglobin measuring unit configured to measure the ratio of a content of glycohemoglobin to a content of hemoglobin in the specimen from the first measurement sample; and
a glucose measuring unit configured to measure the concentration of glucose of the specimen from the second measurement sample, wherein
the glucose measuring unit comprises an enzyme electrode for the measurement of the concentration of glucose,
the preparation unit comprises a dilution bath,
the blood analysis apparatus further comprises a sample injection valve for introducing the first measurement sample prepared in the dilution bath of the preparation unit to the glycohemoglobin measuring unit, a pipe for connecting the sample injection valve and the dilution bath, and a sample introducing pump for introducing the first measurement sample from the dilution bath to the sample injection valve,
the enzyme electrode is provided at the dilution bath, and
the dilution bath is connected to a drain system via an open/close valve that is provided at an upper part of the dilution bath, wherein the open/close valve, when in an opened state, causes excessively supplied cleaning fluid to be discarded to the drain system when the cleaning fluid is supplied to the dilution bath.

2. The blood analysis apparatus according to claim 1, wherein the measurement sample is prepared by the preparation unit by diluting the specimen with a diluent.

3. The blood analysis apparatus according to claim 2, wherein the diluent is also used as the cleaning fluid of a flow path through which the measurement sample moves.

4. The blood analysis apparatus according to claim 3, wherein the diluent contains a supporting electrolyte.

5. The blood analysis apparatus according to claim 3, wherein the diluent has a buffering ability.

6. The blood analysis apparatus according to claim 3, wherein the diluent contains an antiseptic.

7. The blood analysis apparatus according to claim 6, wherein the antiseptic is Na azide.

8. The blood analysis apparatus according to claim 3, wherein the blood sample that the blood analysis apparatus is configured to analyze contains blood cells.

9. The blood analysis apparatus according to claim 8, wherein the diluent contains a surface acting agent for hemolyzing the blood cells.

10. The blood analysis apparatus according to claim 8, wherein the preparation unit includes a stirring unit configured to completely or almost completely hemolyze the blood cells when diluting the specimen.

11. The blood analysis apparatus according to claim 8, wherein the preparation unit includes a stirring unit configured to stir the blood sample to make the blood cell concentration in the specimen uniform.

12. The blood analysis apparatus according to claim 1, wherein the concentration of glucose is measured using an enzyme electrode method.

13. The blood analysis apparatus according to claim 1, further comprising a temperature adjustment unit for simultaneously controlling temperatures of the enzyme electrode and the glycohemoglobin measuring unit.

14. The blood analysis apparatus according to claim 1, wherein the glycohemoglobin measuring unit is configured to measure the ratio of a content of glycohemoglobin to a content of hemoglobin in the specimen using a liquid chromatography method.

15. The blood analysis apparatus according to claim 14, wherein the blood analysis apparatus is configured to simultaneously measure a hemoglobin concentration of the whole blood sample and correct the glucose whole blood measurement result to the plasma conversion value using the hemoglobin concentration.

16. The blood analysis apparatus according to claim 15, wherein the hemoglobin concentration is obtained based on a chromatogram obtained in the measurement of the ratio of a content of glycohemoglobin to a content of hemoglobin in the specimen.

17. The blood analysis apparatus according to claim 1, wherein the blood analysis apparatus outputs a measurement result of the concentration of glucose and a measurement result of the ratio of glycohemoglobin are simultaneously for every patient.

18. The blood analysis apparatus according to claim 1, wherein the blood analysis apparatus measures the concentration of glucose first, and then the blood analysis apparatus measures the ratio of a content of the glycohemoglobin to a content of hemoglobin in the specimen.

19. The blood analysis apparatus according to claim 18, wherein the blood analysis apparatus makes a determination of whether to perform or cancel the measurement of the ratio of a content of glycohemoglobin to a content of hemoglobin in the specimen based on a measurement result of the concentration of glucose.

20. The blood analysis apparatus according to claim 19, wherein the blood analysis apparatus makes a determination on whether to perform or cancel the measurement of the ratio of a content of glycohemoglobin to a content of hemoglobin in the specimen based on a disease type classification flowchart in a diagnosis of diabetes.

21. The blood analysis apparatus according to claim 20, wherein the blood analysis apparatus makes a determination result of the disease classification of the diabetes is simultaneously output with the measurement result of the concentration of glucose and the measurement result of the ratio of a content of glycohemoglobin to a content of hemoglobin in the specimen.

22. The blood analysis apparatus according to claim 1, wherein
the preparation unit is configured to dilute and prepare the specimen to produce the measurement sample, the specimen being simultaneously diluted and prepared by the preparation unit for measuring a concentration of glucose of the specimen and for measuring a ratio of a content of glycohemoglobin to a content of hemoglobin in the specimen by one sample preparation;
the glycohemoglobin measuring unit is configured to measure the ratio of glycohemoglobin of the specimen from a first portion of the measurement sample; and
the glucose measuring unit is configured to measure the concentration of glucose of the specimen from a second portion of the measurement sample.

23. The blood analysis apparatus according to claim 1, wherein
the blood analysis apparatus is configured to use a whole blood sample for the blood sample, and
the blood analysis apparatus is configured to correct a glucose whole blood measurement result to a plasma conversion value using the ratio of a content of glycohemoglobin to a content of hemoglobin in the specimen.

24. The blood analysis apparatus according to claim 1, wherein the dilution bath is further connected to the drain system via an open/close valve that is provided at a bottom part of the dilution bath.

* * * * *